United States Patent [19]
Bolton

[11] Patent Number: 6,086,552
[45] Date of Patent: *Jul. 11, 2000

[54] TREATMENT OF CHRONIC POST-TRAUMATIC PAIN SYNDROMES

[75] Inventor: Anthony E. Bolton, Tideswell, United Kingdom

[73] Assignee: Vasogen, Inc., Mississauga, Canada

[ * ] Notice: This patent is subject to a terminal disclaimer.

[21] Appl. No.: 09/090,465

[22] Filed: Jun. 4, 1998

[51] Int. Cl.$^7$ ............................. A61M 37/00; A61B 19/00
[52] U.S. Cl. ................................... 604/4; 128/898
[58] Field of Search ................... 604/4; 422/44; 128/898; 210/758, 760

[56] References Cited

U.S. PATENT DOCUMENTS

| | | |
|---|---|---|
| 4,968,483 | 11/1990 | Muller et al. . |
| 5,591,457 | 1/1997 | Bolton . |
| 5,834,030 | 11/1998 | Bolton ................................ 424/613 |

FOREIGN PATENT DOCUMENTS

| | | |
|---|---|---|
| 2191940 | 6/1996 | Canada . |
| 2206180 | 11/1998 | Canada . |
| 4446292 | 12/1994 | Germany . |
| 93/15778 | 8/1993 | WIPO . |
| 93/15779 | 8/1993 | WIPO . |
| 96/34613 | 11/1996 | WIPO . |
| 98/07436 | 2/1998 | WIPO . |

OTHER PUBLICATIONS

Bolton, Treatment of severe Raynaud's syndrome by injection of autologous blood pretreated by heating, ozonation and exposure to ultraviolet light, International Angiology, 1997, vol. 16/4, pp. 250–264.

Bolton, Effect of combinedheat, ozonation and ultraviolet irradiation on heat shock protein expression by peripheral blood leukocyte populations, J. Biol. Regul. Homeostatic Agents, 1997, vol. 11/3, pp. 104–110.

Baran et al, Mueller Medical Int'l, Inc., Oakville, Ontario, Canada (1990).

*Primary Examiner*—Mark O. Polutta
*Assistant Examiner*—Patricia M. Bianco
*Attorney, Agent, or Firm*—Nixon & Vanderhye

[57] ABSTRACT

Reflex sympathetic dystrophy in a human patient is treated by collecting an aliquot of the patient's blood (e.g. 10 cc in volume), and subjecting it simultaneously to ozone/oxygen mixture and ultraviolet light, at a predetermined, elevated (e.g. 42.5° C.) temperature, for approximately 3 minutes. After cooling, the treated blood aliquot is reinjected into the patient via the gluteal muscle. Reflex sympathetic dystrophy is alleviated following a course of such treatments.

7 Claims, No Drawings

TREATMENT OF CHRONIC POST-TRAUMATIC PAIN SYNDROMES

FIELD OF THE INVENTION

This invention relates to methods of medical treatment, and more specifically to the treatment of reflex sympathetic dystrophy.

BACKGROUND OF THE INVENTION

Reflex sympathetic dystrophy (RSD) is a pathogenic condition affecting a patient's extremities and characterized by persistent pain and swelling with vasomotor and sudomotor changes, and later atrophy. The precipitating cause of RSD is soft tissue injury. Fractures of the bones of the wrists are commonly associated with RSD. Chronic undiagnosed knee pain, with few clinical signs beyond hyperaesthesia and limited movement may suggest RSD. It may only manifest itself days, weeks, or even years after the soft tissue injury has been incurred.

Adopting clinical criteria, the following operational definition of RSD was adopted at the Sixth World congress of Pain:

"RSD is a descriptive term meaning a complex disorder or group of disorders that may develop as a consequence of trauma affecting the limbs, with or without an obvious nerve lesion. RSD may also develop after visceral diseases, and central nervous system lesions or, rarely, without an obvious antecedent event. It consists of pain and related sensory abnormalities in the motor system and changes in structure of both superficial and deep tissues ("trophic changes"). It is not necessary that all components are present. It is agreed that the name "reflex sympathetic dystrophy" is used in a descriptive sense and does not imply specific underlying mechanisms".

The pathogenesis and pathophysiology of reflex sympathetic dystrophy are most commonly characterized by impaired vasomotor control which usually results in vasodilation and increased skin temperature over the affected area, in the initial stages, and vasoconstriction and reduced skin temperature in the later stages. Also, the blood flow and skin temperature changes in the contralateral limb following cold stress of the affected limb are abnormal, thus suggesting a central nervous system abnormality.

There is currently no specific, accepted treatment for RSD, and cure of it cannot be assured. Vascular and perhaps neurological changes occur during the natural history of the disease. Some treatments are directed to those. For example, calcitonin, a vasoconstrictor, is often used during the early vasodilation stage, but is inappropriate at later stages when vasoconstriction predominates. In this stage, pharmacologic or surgical sympathectomy is effective in some cases. Immobilization of the affected limb is avoided, since this exacerbates the problem. Alternative therapies include corticosteroids, transcutaneous nerve stimulation, acupuncture and autogenic training.

REFERENCE TO THE PRIOR ART

A review of reflex sympathetic dystrophy by Dr. E. D. Cooke, Thermographic and Blood Flow Unit, St. Bartholomew's Hospital, London, U.K., appears in "Vascular Medicine Review", 1994; 5: 319–330.

SUMMARY OF THE INVENTION

It is an object of the present invention to provide a novel treatment for reflex sympathetic dystrophy.

According to the present invention, the treatment for alleviating reflex sympathetic dystrophy, RSD, involves extracting an aliquot of blood of a patient suffering from RSD and treating it (either as whole blood or the appropriate fraction thereof) with certain stressors, namely UV radiation, heat and an oxidative environment. The aliquot so treated is reinjected intramuscularly into the patient. Following one or more such treatments, spaced at appropriate intervals, alleviation of the RSD is experienced.

Another aspect of the present invention is an autologous blood aliquot for administration to a patient to alleviate RSD, the aliquot having a volume of from about 0.01 ml to about 400 ml, and being characterized by the presence therein, in comparison with normal blood of the patient from whom it was extracted, of at least one of the following characterizing features:

increased numbers of lymphocytes and other leucocytes, exhibiting a condensed apoptotic-like morphology;

a release of specific proteins from the cell surface of the blood leucocytes, including the MHC Class II molecule HLA-DR, resulting in a reduction in the number of cells expressing such surface proteins;

an upregulation in the expression of certain cell surface markers for example CD-11b, a component of the ligand for the cell adhesion molecule ICAM-1;

a decrease in the amount of heat shock protein HSP-60 contained in the leucocytes, particularly the lymphocytes, therein, and an increase in HSP-60 in the plasma;

a decrease in HSP-72 within the lymphocytes;

a decrease in proliferation of treated mononuclear cells following mitogenic stimulation.

DESCRIPTION OF THE PREFERRED EMBODIMENTS

By inducing an apoptotic-like state in the lymphocytes and other leucocytes in the blood comprising the aliquot, as evidenced by the increased numbers of lymphocytes and other leucocytes exhibiting a condensed apoptotic-like morphology therein, these cells may become preferentially phagocytosed upon re-injection into the host body.

There are a number of different phagocytic cell types present in the mammalian body, including various antigen presenting cells and neutrophils. In order to facilitate phagocytosis by antigen presenting cells rather than by other phagocytes, the lymphocytes and other leucocytes present in the aliquot of the invention are treated so that they may interact preferentially with antigen presenting phagocytic cells. Cells adhere to each other by a number of mechanisms including the expression of cell adhesion molecules. Cell adhesion molecules present on one cell type interact with specific ligands for particular adhesion molecules present on the adhering cell type. The present invention may result in a preferential interaction of cells in the treated aliquot to antigen presenting cells in the host body, by upregulation, on the surface of the cells in the treated aliquot of the expression of the ligand for adhesion molecules found on antigen-presenting cells in the host body. Antigen presenting cells express a number of cell adhesion molecules, including ICAM-1, a component of the ligand of which is CD-11b. One way by which the process of the invention may change the preferential phagocytosis of apoptosing cells is by upregulation of CD-11b.

The preparation of the blood aliquot for use according to the present invention preferably comprises extracting from the patient an aliquot of blood of volume about 0.01 ml to about 400 ml, and contacting the aliquot of blood, extracorporeally, with an effective amount of ozone gas and ultraviolet radiation.

The treatment for the alleviation of reflex sympathetic dystrophy, RSD, in a human patient suffering therefrom, in accordance with preferred embodiments of the present invention, comprises extracting from the patient an aliquot of blood of volume about 0.01 ml to about 400 ml, contacting the aliquot of blood, extracorporeally, with an effective amount of ozone gas, heat and ultraviolet radiation, followed by administering the treated blood aliquot to the human patient.

In the preferred blood aliquot used in the present invention, the number of mononuclear cells or leucocytes exhibiting the presence of RSP-60 therein is decreased, as is the amount of HSP-60 in each cell, as compared with the normal, untreated peripheral blood of the source patient. Whereas the patient normally has, typically, about 30% of mononuclear cells exhibiting the presence of HSP-60 therein (as measured by whole blood intracellular flow cytometry), the treated aliquot has only 12–20%, In clinical studies, it has been found that the figure reduces from 29.3% to 15.5%, mean of six tests, Preferably also, the number of leucocytes exhibiting the presence of HSP-72, which is about 50% in the untreated blood of the source patient, is reduced to 25–35% in the treated aliquot of the present invention. In clinical studies, this figure for HSP-72 reduced from 49.4% in untreated blood to 30.2% in the treated aliquot, mean of six tests, similarly measured.

The number of cells which express the cell surface specific protein HLA-DR, in the preferred aliquot used in the present invention, is reduced as compared with the patient's untreated blood, possibly as a result of its release from the cell surface. Typically, the number of cells expressing HLA-DR reduces from about 23% to about 8–12%, as measured by whole blood flow cytometry. In clinical studies, this figure reduced from 23.3% to 10.3%, mean of five experiments.

The upregulation of the surface marker CD-11b in the preferred aliquot used in the present invention can be expressed as an increase in the percentage of neutrophils in the aliquot which test positive for CD-11b, compared with the patient's source blood. Typically, the increase is from about 10% up to the approximate range 70–95%. In clinical studies, an increase from 10.3% to 84% was obtained, mean of six tests.

A significant feature of the present invention is that the source of the blood from which the aliquot is prepared for a specific patient is the patient himself or herself. The antigens forming the basis of the aliquot find their origin in the patients own blood. No extraneous antigens are added; the effective antigens are present in the patient's blood, and/or are released or modified by the process of preparing the aliquot using the patients' own blood as the source material.

The treated aliquot is prepared by extracting the patient's venous blood into an anticoagulant such as sodium citrate (a standard, routine procedure), and then exposing the extracted blood aliquot to at least one stressor, in controlled amounts, the stressor being selected from among oxidizing agents such as ozone, ultraviolet radiation and elevated temperature, and combinations of two or more of such stressors. The resulting blood aliquot, after such treatment, can be reinjected into the patient. Following a course of such treatments, a patient's RSD may be markedly improved.

Preferably, the stressors to which the leucocytes in the extracted blood aliquot are subjected are a temperature stress (blood temperature above body temperature), an oxidative environment, such as a mixture of ozone and oxygen bubbled through the blood aliquot, and ultraviolet radiation, simultaneously or successively, but preferably simultaneously.

The preferred embodiments of the present invention provide a method of alleviating reflex sympathetic dystrophy in a human patient, which comprises:

(a) contacting of about 0.01 ml to about 400 ml of the human patient's blood with an effective amount of ozone gas and ultraviolet radiation; and (b) administering the blood treated in step (a) to the human patient.

In general, from about 0.01 ml to about 400 ml of blood may be treated according to the invention. Preferred amounts are in the range of about 0.1 ml to 200 ml. More suitably, the aliquot for treatment has a volume of from about 0.1–100 mls, preferably 1–50 ml and most preferably 5–15 mls. The method most preferably involves collecting 10 ml of a patient's venous blood into sodium citrate coagulant, transferring it to a sterile, disposable low-density polyethylene vessel, and then treating it with ozone gas and ultraviolet radiation, then re-administering the treated blood to the patient by intramuscular injection.

As noted, it is preferred, according to the invention, to apply all three of the aforementioned stressors simultaneously to the aliquot under treatment. Care must be taken not to utilize an excessive level of the stressors, to the extent that the cell membranes of the white cells are caused to be disrupted.

The temperature stressor must keep the aliquot in the liquid phase, i.e. from about 0° C. to about 56° C. and should not heat it above about 55° C. Any suitable source of heat known in the art may be employed to heat the blood, preferably one or more infrared lamps. Preferably the temperature stressor warms the aliquot being treated, to a temperature above normal body temperature, i.e. to about 37–45° C, and most preferably from about 37–43° C., e.g. about 42.5° C. Preferably the temperature of the blood aliquot is maintained at this elevated temperature during the treatment with UV/ozone.

Alternatively, the blood sample is heated while being subjected to UV radiation, until the blood reaches a predetermined temperature (preferably about 42.5° C.), at which point bubbling of ozone gas through the blood is commenced. The concurrent UV/ozone treatment is then maintained for a predetermined period of time, preferably about 3 minutes.

Another alternative method involves subjecting is the blood to UV/ozone while heating to a predetermined temperature (preferably about 42.5° C.), then either ending the treatment once the predetermined temperature is reached, or continuing UV/ozone treatment for a further period of time, most preferably about 3 minutes.

The application of the oxidative stressor preferably involves exposing the aliquot to a mixture of medical grade oxygen and ozone gas, most preferably by bubbling through the aliquot, at the aforementioned temperature range, a stream of medical grade oxygen gas having ozone as a minor component therein. The ozone gas may be provided by any conventional source known in the art. Suitably the gas stream has an ozone content of from about 1.0–100 $\mu$g/ml, preferably 3–70 $\mu$g/ml, and most preferably from about 5–50 $\mu$g/ml. The gas stream is supplied to the aliquot at a rate of from about 0.01–2.0 liters per minute, preferably 0.1–1.0 liters per minute and most preferably at about 0.12 liters per minute (STP).

The ultraviolet radiation stressor is suitably applied by irradiating the aliquot under treatment from an appropriate source of UV radiation, while the aliquot is maintained at the aforementioned temperature and while the oxygen/ozone gaseous mixture is being bubbled through the aliquot. The ultraviolet radiation may be provided by any conventional source known in the art, for example by a plurality of low-pressure ultraviolet lamps. The method of the invention preferably utilizes a standard UV-C source of ultraviolet radiation, namely UV lamps emitting in the C-band wavelengths, i.e. at wavelengths shorter than about 280 nm. Ultraviolet radiation corresponding to standard UV-A and UV-B sources can also be used. Preferably employed are low-pressure ultraviolet lamps that generate a line spectrum wherein at least 90% of the radiation has a wavelength of about 253.7 nm, An appropriate dosage of such UV radiation, applied simultaneously with the aforementioned temperature and oxidative environment stressors, is obtained from lamps with a power output of from about 5 to about 25 watts, preferably about 5–10 watts, at the chosen UV wavelength, arranged to surround the sample container holding the aliquot. Each such lamp provides an intensity, at a distance of 1 meter, of from about 40–80 microwatts per square centimeter. Several such lamps surrounding the sample bottle, with a combined output at 253.7 nm of 15–40 watts, preferably 20–40 watts operated at maximum intensity, may advantageously be used. At the incident surface of the blood, the UV energy supplied may be from about 0.25–4.5 Joules per $cm^2$ during a 3-minute exposure, preferably 0.9–1.8 $J/cm^2$. Such a treatment provides a blood aliquot which is appropriately modified according to the invention to create the treated aliquot outlined above ready for re-injection into the patient.

The time for which the aliquot is subjected to the stressors can be from a few seconds to about 60 minutes. It is normally within the time range of from about 0.5–60 minutes. This depends to some extent upon the chosen intensity of the UV irradiation, the temperature and the concentration of and rate at which the oxidizing agent is supplied to the aliquot. The more severe the stressors applied to the aliquot, generally the shorter time for which they need to be applied. Some experimentation to establish optimum times may be necessary on the part of the operator, once the other stressor levels have been set. Under most stressor conditions, preferred times will be in the approximate range of about 0.5–10 minutes, most preferably 2–5 minutes, and normally around 3 minutes. The starting blood temperature, and the rate at which it can be warmed or cooled to a predetermined temperature, tends to vary from patient to patient.

In the practice of the preferred process of the present invention, the blood aliquot (or the separated cellular fractions of the blood, or mixtures of the separated cells, including platelets, these various leucocyte-containing combinations, along with whole blood, being referred to collectively throughout as the "aliquot") may be treated with the stressors using an apparatus of the type described in U.S. Pat. No. 4,968,483 Mueller. The aliquot is placed in a suitable, sterile, UV-radiation-transmissive container, which is then fitted into the machine. The temperature of the aliquot is adjusted to the predetermined value, e.g. 42.5° C., by the use of a suitable heat source such as an IR lamp, and the UV lamps are switched on for a fixed period before the gas flow is applied to the aliquot providing the oxidative stress, to allow the output of the UV lamps to stabilize. Then the oxygen/ozone gas mixture, of known composition and controlled flow rate, is applied to the aliquot, for the predetermined duration of 0.5–60 minutes, preferably 2–5 minutes and most preferably about 3 minutes as discussed above, so that the aliquot experiences all three stressors simultaneously. In this way, the blood aliquot is appropriately modified to produce a treated aliquot according to the present invention sufficient to achieve the desired treatment of reflex sympathetic dystrophy.

The invention is further described in the following working example.

EXAMPLE

A young (32 year old) adult female suffering from reflex sympathetic dystrophy was treated according to the process of the invention.

The patient's RSD manifested itself as extremely cold feet, with numerous small wounds (chilblains) on the feet. Even during hot summer weather, the patient experienced problems with foot pains. The patient was given a course of treatment according to the invention. At each treatment, a 10 ml aliquot of blood was withdrawn from the patient, and the blood aliquot was subjected to simultaneous treatment with an ozone/oxygen gaseous mixture (15±0.6 $\mu g/ml$ of ozone) and ultraviolet light, for 3 minutes, at 42.5° C., in an apparatus as described in U.S. Pat. No. 4,968,483 Mueller. An IR lamp was use to heat the sterile container holding the blood liquot to the preselected temperature. Ultraviolet radiation was supplied from a plurality of UV emitting lamps surrounding the container, the lamps providing a combined output at 253.7 nm wavelength of 0.26 Joules per $cm^2$ at the incident surface of the blood. After the treated aliquot had reverted to body temperature, it was re-injected intramuscularly into the patient, via the gluteal muscle.

The patient received initially a course of nine such treatments, three times weekly for three weeks. She reported improvement by the end of this initial course. After a three week interval, the patient reported that the improvement was lessening, and so she was given a further course of nine treatments over three weeks. The improvement resumed. After a 1–2 week break, after which signs of lessening of the improvement were reported by the patient, treatments were resumed on a twice per week basis for 6 weeks, followed by one per week for 4 weeks.

The patient reported a substantial alleviation, almost complete cure, of her RSD symptoms following the completion of these courses of treatments.

What is claimed is:

1. A process of alleviating the symptoms of reflex sympathetic dystrophy in a human patient suffering therefrom, which comprises:

extracting an aliquot of blood of volume from about 0.1 to 400 ml from the human patient;

treating the extracted aliquot extracorporeally with at last one stressor selected from a group of an oxidative environment, UV radiation and elevated temperature up to about 45° C. for a period of time in the range 0.5–60 minutes:

and reinjecting the aliquot so treated into the human patient.

2. The process of claim 1 wherein the aliquot of blood is subjected to all three said stressors simultaneously.

3. The process of claim 2 wherein the oxidative environment stressor is a mixture of medical grade oxygen and ozone, wherein the ozone content is from 0.1 to 100 $\mu g/ml$, bubbled through the blood aliquot.

4. The process of claim 2 wherein the ultraviolet radiation stressor is ultraviolet radiation from UV lamps emitting primarily at wavelengths of 280 nm or shorter.

5. The process of claim 2 wherein the elevated temperature stressor is a temperature in the range from 38–43° C.

6. A process of alleviating the symptoms of reflex sympathetic dystrophy in a human patient suffering therefrom, which comprises:

extracting an aliquot of blood of volume from about 0.1 to 400 ml from the human patient;

treating the extracted aliquot extracorporeally simultaneously with an oxidative environment consisting essentially of a mixture of medical grade oxygen and ozone, wherein the ozone content is from 0.1 to 100 µg/ml, bubbled through the blood aliquot;

ultraviolet radiation from UV lamps emitting primarily at wavelengths of 280 nm or shorter;

and an elevated temperature in the range from about 38–43° C.; for a period of time in the range of 0.5–60 minutes; and reinjecting the aliquot so treated into the human patient.

7. A process of alleviating the symptoms of reflex sympathetic dystrophy in a human patient suffering therefrom, which comprises subjecting the patient to a course of from 18 to 34 treatments as defined in claim 6, over a period of 6–21 weeks.

* * * * *